United States Patent
Broadus et al.

(10) Patent No.: US 6,231,186 B1
(45) Date of Patent: May 15, 2001

(54) EYE MEASUREMENT SYSTEM

(75) Inventors: Charles R. Broadus, Bothell, WA (US); Timothy N. Turner, West Jordan, UT (US)

(73) Assignee: Bausch & Lomb Surgical, Inc., Claremont, CA (US)

( * ) Notice: Subject to any disclaimer, the term of this patent is extended or adjusted under 35 U.S.C. 154(b) by 0 days.

(21) Appl. No.: 09/535,410

(22) Filed: Mar. 24, 2000

(51) Int. Cl.[7] .................................................. A61B 3/14
(52) U.S. Cl. ......................................................... 351/208
(58) Field of Search .................................. 351/205, 206, 351/208, 212, 221, 160 R, 211, 214; 623/4.1, 6.11, 6.26; 356/496, 497, 512; 606/4

(56) References Cited

U.S. PATENT DOCUMENTS

| 4,764,006 | | 8/1988 | Hamano et al. .................. 351/211 |
| 5,116,114 | * | 5/1992 | Nakamura et al. ................ 351/205 |
| 5,728,156 | * | 3/1998 | Gupta et al. ....................... 351/160 R |

* cited by examiner

Primary Examiner—George Manuel
(74) Attorney, Agent, or Firm—Michael L. Smith

(57) ABSTRACT

An eye measurement system (10) includes a biometric ruler (14) and an anterior segment analyzer (12) where the system (10) compares a biometric ruler measurement to an anterior segment analyzer measurement to correct for any error in the biometric ruler measurement.

14 Claims, 1 Drawing Sheet

EYE MEASUREMENT SYSTEM

FIELD OF INVENTION

The present invention generally relates to a system for measuring the total axial distance of an eye. More specifically, the present invention relates to a system where the measurements of a biometric ruler are combined with the measurement of an anterior segment analyzer.

DESCRIPTION OF RELATED ART

Biometric rulers, also commonly known as A-scan devices or ultrasonic probes, are well known in the art. These devices typically transmit an ultrasonic pulse through a probe device which is in contact with the patient's cornea. The pulse waves are reflected back from the components of the eye and received by the ruler. The time it takes for certain echo reflections to be received can be related to distance values through well known equations.

An error in the measurement of the total axial length of the eye with the biometric ruler is often introduced by the need for the probe transducer to contact the cornea surface. This contact often causes a slight depression or flattening of the cornea, which introduces error into the distance measurements of the biometric ruler. The anterior segment analyzer, on the other hand, does not require any contact with the cornea surface and therefore its measurements are not subject to the error of the biometric ruler.

However, the anterior segment analyzer cannot provide a distance measurement to the posterior surface of the lens or the retina and therefore cannot give a complete axial length measurement to each particular surface along the axial length of an eye.

It is also known to use an ultrasonic transducer in combination with a ultrasound gel such that the probe can be held above the cornea without depressing it. If the cornea is not depressed an accurate axial distance measurement of the eye can be achieved but it is very uncomfortable and messy for the patient.

Therefore, a need exists to provide a system that would eliminate the error introduced by the use of the biometric ruler and yet provide distance measurement information in a quick convenient manner.

DETAILED DESCRIPTION OF THE INVENTION

Figure 1:
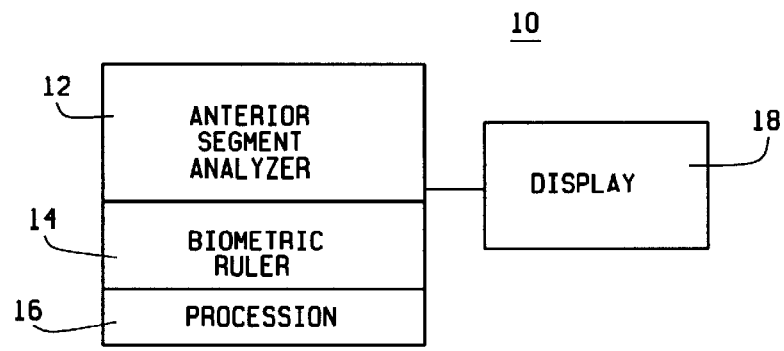
FIG. 1 is a block diagram of a system in accordance with the present invention.

An eye measurement system 10, in accordance with the present invention is disclosed in FIG. 1. System 10 includes an anterior segment analyzer 12, a biometric ruler 14, a processor 16, and a display 18.

The anterior segment analyzer 12 is preferably an elevation-based topography system such as the ORBSCAN® System available from Bausch & Lomb Surgical, Inc. However, anterior segment analyzer 12 may also be any that can obtain at least the axial distance measurements of the anterior segment of an eye, without the need for contacting the anterior corneal surface. That is to say, the anterior segment analyzer 12 needs to provide at least a distance from the anterior corneal surface to the anterior lens surface. The anterior segment analyzer 12 also preferably provides the corneal thickness, and distance measurements from the anterior corneal surface to the anterior surface of the iris. The analyzer 12, such as the preferred ORBSCAN system, is preferably a slit-lamp based, corneal and anterior segment topography system that simultaneously measures both surfaces of the cornea as well as the anterior of the lens and iris. Each measured surface can be displayed on display 18. For illustrative descriptions of the elevation-based ORSCAN topography system, see U.S. Pat. Nos. 5,512,965 and 5,512,966 by Richard K. Snook.

Biometric ruler 14 is preferably an ultrasonic system commonly known as A-scan device and of the type described in U.S. Pat. No. 4,564,018. The ruler 14 typically includes a probe 20 (shown in FIG. 2) that must come in contact with the cornea of an eye and which sends an ultrasonic pulse through the eye to obtain an axial distance, which includes at least a measurement of the anterior chamber depth, a lens thickness, and a vitreous distance of the eye. The anterior chamber depth of a patient's eye is defined as the distance from the anterior surface of the cornea to the anterior surface of the lens, a lens thickness is defined as the distance from the anterior surface of the lens to the posterior surface of the lens, and a vitreous distance is defined as the distance from the posterior surface of the lens to the retina. The biometric ruler 14 can easily introduce error in the measurement of the anterior chamber depth as described in more detail below.

In order to eliminate the error introduced by the biometric ruler 14 measurement of the anterior chamber depth processor 16 combines the anterior chamber depth measurement of analyzer 12 with the lens thickness and vitreous distance measurements of ruler 14 to provide a complete and accurate axial length distance measurement of an eye to a physician on display 18. Processor 16 is preferably a processing unit of a system such as the ORBCAN in combination with a biometric ruler 14. The processor 16 can be any type of processor capable of combining the measurements of the analyzer 12 with the measurements of the ruler 14.

A valuable consequence of the inventive system 10 is that the use of messy and uncomfortable ultrasonic gels and water baths on the eye may be eliminated by making the measurements through the eyelid (not shown) of a patient. Also, by measuring through the eye no anethesia is needed to be applied to the eye, thus saving time. All of this greatly reduces the discomfort and inconvenience. It is noted that not all biometric ruler 14 measurements will be able to be made through the eyelid of a patient. The ruler 14 requires that the ultrasonic pulse be aimed in a straight-line from the cornea through the pupil to the retina. It is believed that when some patients close their eyes, the eye may drift off-axis making it difficult for a user of ruler 14 to obtain an acceptable measurement through the eyelid.

Processor 16 preferably can simply take the anterior chamber depth measurement of analyzer 12 and add it to the lens thickness and vitreous distance measurements of ruler 14. Or processor 16 can compare the anterior chamber depth measurement of analyzer 12 with the ruler 14 anterior chamber depth measurement to assure that ruler 14's measurement is within some statistically insignificant threshold. A threshold limit might be on the order of 20–30 microns. Additionally, the system 10 could be programmed to add any additional length of the anterior chamber depth measured by analyzer 12 to the anterior chamber depth measurement of ruler 14.

Figure 2:
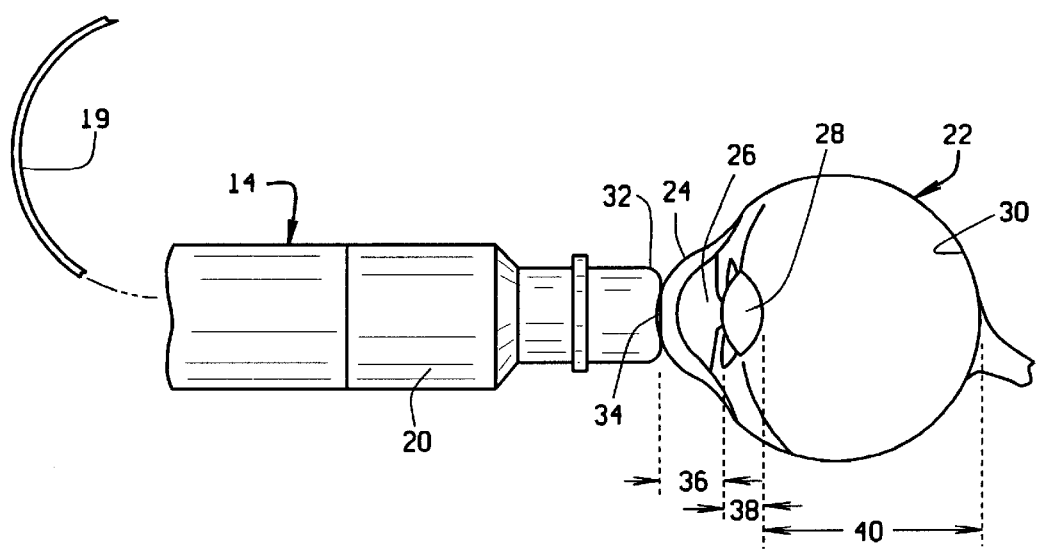
FIG. 2 is a diagram showing the use of a biometric ruler.

FIG. 2 shows a biometric ruler 14 with a probe 20 in contact with an eye 22, where line 19 is connected to system 10. Eye 22 includes a cornea 24, an anterior chamber 26, a lens 28, and a retina 30. The end 32 of probe 20 causes a flattening of cornea 24, as shown at 34, which introduces error into all of ruler 14's measurements. Ruler 14 then obtains an anterior chamber depth measurement 36, a lens thickness 38, and a vitreous distance 40. The measurements 36, 38, and 40 are then combined to provide an axial distance measurement of the eye 22.

Thus, there has been described a system for providing a complete and accurate axial distance measurement of the eye.

What is claimed is:

1. An eye measurement system comprising:
    a biometric ruler for obtaining at least a measurement of an anterior chamber depth of a patient's eye, a lens thickness of the eye, and a vitreous distance of the eye;
    an anterior segment analyzer for obtaining at least a measurement of the anterior chamber depth of the eye; and
    wherein the system compares the biometric ruler anterior chamber depth measurement to the anterior segment analyzer anterior chamber depth measurement to correct any error in the biometric rule anterior chamber depth measurement.

2. The system of claim 1 wherein the biometric ruler is an ultrasonic device.

3. The system of claim 1 wherein the anterior segment analyzer is an elevation-based topography system such as an OBSCAN® System.

4. The system of claim 1 wherein the biometric ruler measurements are obtained through an eyelid of the patient thereby minimizing any discomfort or inconvenience of the patient.

5. An eye measurement system for obtaining a linear measurement of a patient's eye, comprising:
    a measurement of an anterior chamber depth, a lens thickness, and a vitreous distance;
    an anterior segment analyzer for a measurement of the anterior chamber depth; and
    wherein the system combines the anterior segment analyzer's anterior chamber depth measurement with the biometric ruler's lens thickness, and vitreous distance measurements to present a physician with a highly accurate and complete axial distance measurement of the eye.

6. The system of claim 5 wherein the biometric ruler is an ultrasonic device.

7. The system of claim 5 wherein the anterior segment analyzer is an elevation-based topography system such as an ORBSCAN® System.

8. The system of claim 5 wherein the biometric ruler measurements are obtained through an eyelid of the patient thereby minimizing any discomfort or inconvenience of the patient.

9. An eye measurement system comprising:
    a biometric ruler for obtaining a measurement of a lens thickness of an eye and a vitreous distance of the eye;
    an anterior segment analyzer for obtaining a measurement of an anterior chamber depth of the eye; and
    a processing unit operatively connected to the biometric ruler and the anterior segment analyzer wherein the processing unit combines the anterior chamber depth measurement with the lens thickness and vitreous distance measurements for providing a physician an accurate, complete axial distance measurement of the eye.

10. The system of claim 9, wherein the biometric ruler is an ultrasonic device.

11. The system of claim 9 wherein the anterior segment analyzer is an elevation-based topography system such as an ORBSCAN® System.

12. The system of claim 9 wherein the biometric ruler measurements are obtained through an eyelid of the patient thereby minimizing any discomfort or inconvenience of the patient.

13. A method of measuring an axial distance of a patient's eye comprising the steps of:
    measuring a lens thickness and a vitreous distance of the eye using a biometric ruler;
    measuring an anterior chamber depth of the eye using an anterior segment analyzer;
    combining the measurements, in a processor connected to the biometric ruler and the anterior segment analyzer; and
    providing the combined measurements to a physician as an accurate, complete axial distance of the eye.

14. The method of claim 13 further including the step of obtaining the biometric ruler measurements through an eyelid of the patient.

* * * * *